United States Patent

Kadowaki et al.

Patent Number: 5,238,899
Date of Patent: Aug. 24, 1993

[54] ACTIVE CARBON FOR DEODORIZATION AND PROCESS FOR PREPARATION THEREOF

[75] Inventors: Satoru Kadowaki, Mie; Makoto Suzuki, Kariya; Kunio Okamoto; Atushi Kosaka, both of Okazaki, all of Japan

[73] Assignees: Nippondenso Co., Ltd., Kariya; Nippon Soken, Inc., Nishio, both of Japan

[21] Appl. No.: 792,261

[22] Filed: Nov. 15, 1991

[30] Foreign Application Priority Data

Nov. 16, 1990 [JP] Japan ................... 2-308633

[51] Int. Cl.$^5$ .............. B01J 20/22; B01J 20/20; B01D 53/02; A61L 9/00
[52] U.S. Cl. ............. 502/401; 422/4; 422/5; 502/413; 502/417; 95/90; 95/141
[58] Field of Search ......... 502/413, 417, 437, 401, 502/158

[56] References Cited

U.S. PATENT DOCUMENTS

| | | | |
|---|---|---|---|
| 3,985,928 | 10/1976 | Watanabe et al. | 427/386 |
| 4,443,354 | 4/1984 | Eian | 502/401 |
| 4,460,640 | 7/1984 | Chi | 427/387 |
| 4,810,266 | 3/1989 | Zinnen et al. | 55/68 |
| 4,831,011 | 5/1989 | Oikawa et al. | 502/406 |
| 5,084,516 | 1/1992 | Tsuchiya et al. | 525/905 |

FOREIGN PATENT DOCUMENTS

| | | |
|---|---|---|
| 1162904 | 2/1984 | Canada . |
| 0090563 | 10/1983 | European Pat. Off. . |
| 2315950 | 1/1977 | France . |
| 60-202375 | 10/1985 | Japan . |
| 1255199 | 9/1986 | U.S.S.R. ............ 502/413 |

Primary Examiner—Paul E. Konopka
Attorney, Agent, or Firm—Cushman, Darby & Cushman

[57] ABSTRACT

Disclosed is an active carbon for deodorization, which comprises a deodorizing functional group fixed to a graphitic six-membered ring on the surface of the active carbon, through a silanol bond.

11 Claims, 2 Drawing Sheets

ACTIVE CARBON FOR DEODORIZATION AND PROCESS FOR PREPARATION THEREOF

BACKGROUND OF THE INVENTION

1. Field of the Invention

The present invention relates to active carbon used for deodorization, and a process for the preparation thereof. More particularly, the present invention relates to a deodorizing active carbon providing an excellent deodorization of a bad smell in a gas phase, especially a smell of tobacco smoke.

2. Description of the Related Art

In general, active carbon provides an excellent deodorizing of a bad smell in a gas phase, even at a low concentration, and is widely used as a deodorant. Nevertheless, active carbon is defective in that the deodorizing capacity thereof with regard to a component stimulant at a low concentration, such as hydrogen sulfide, acetaldehyde or ammonia, is low. As the means for overcoming this defect, there are known a process in which a low-molecular-weight amine is deposited on active carbon to remove an aldehyde (see Japanese Unexamined Patent Publication No. 60-202735), and a process in which an organic silane compound and an essential oil are added in combination and the smell of hydrogen sulfide or ammonia is removed by utilizing volatile components (see Japanese Unexamined Patent Publication No. 63-168171).

Furthermore, there have been proposed a process in which active carbon is subjected to a low-temperature plasma treatment using an amino group-containing compound such as ammonia or an organic amine, a process in which an amino group is introduced into active carbon by a physical means of an irradiation with energy rays such as ultraviolet rays or electron beams (see Japanese Unexamined Patent Publication No. 62-263377), and a process in which active carbon is treated with ozone, hydrogen peroxide or sulfuric acid to introduce an electron donor functional group into the surface of graphite and a metal ion is coordinated with the graphite to form a chelate structure (Japanese Unexamined Patent Publication No. 62-191040).

Nevertheless, the process of supporting (depositing) a compound having a deodorizing capacity on the surface of active carbon is defective in that, since the deposited substance is not tightly fixed to the carrier, the deposited substance drops off during use or the deposited substance is separated during a wet process, and thus the performance thereof is drastically reduced. Furthermore, according to this process, the deposited substance is adhered unevenly to the carrier, and thus the functional group is not effectively utilized.

The above process of chemically bonding a functional group to the surface of active carbon can be theoretically established, but from the industrial viewpoint, the process is very complicated, and in view of the shape, efficiency and safety, the process cannot be practically applied to a carbon fiber or active carbon. Moreover, it is difficult to introduce the deodorizing component in the form of an effective primary amine, and it is difficult to control a formation of an inactive secondary or tertiary amine, which is not effective, and thus the deodorizing performance is poor.

SUMMARY OF THE INVENTION

An object of the present invention is to provide an active carbon for deodorization, in which, by preparing a functional group having a deodorizing effect and fixing the functional group firmly to the surface of the carrier without any change of the activity of the functional group, even after introduction to the surface of an active carbon, a dropping off of the effective functional group during use and a degradation of the performance by a wet process can be controlled, and since the functional group is regularly fixed, the functional group is utilized more effectively than in the conventional technique, and a process suitable for, industrial production, in which this active carbon can be easily prepared with an improved deodorizing efficiency.

In accordance with one aspect of the present invention, this object can be attained by an active carbon for deodorization, which comprises a deodorizing functional group fixed to a graphitic six-membered ring on the surface of an active carbon, through a silanol bond.

In accordance with another aspect of the present invention, there is provided a process for the preparation of an active carbon for deodorization, which comprises the steps of forming a hydroxyl group on graphitic active carbon on the surface of an active carbon by an oxidation treatment, and condensing the hydroxyl group formed on the surface of the active carbon with a silicon compound having a hydrolyzable group and a deodorizing functional group, to thereby fix the deodorizing functional group to the surface of the active carbon through a silanol bond.

DESCRIPTION OF THE PREFERRED EMBODIMENTS

In the present invention, a silanol bond is utilized for the chemical bonding of a deodorizing functional group to the surface of an active carbon. The silanol bond is formed by dehydration condensation of a silanol group (Si—OH) with a hydroxyl group on the surface of an inorganic material, and therefore, this chemical bond can be easily and stably introduced into the surface of the inorganic material. Accordingly, by using a compound formed by bonding a deodorizing functional group to Si of a silanol group, the deodorizing functional group can be introduced as intended.

Figure 1:
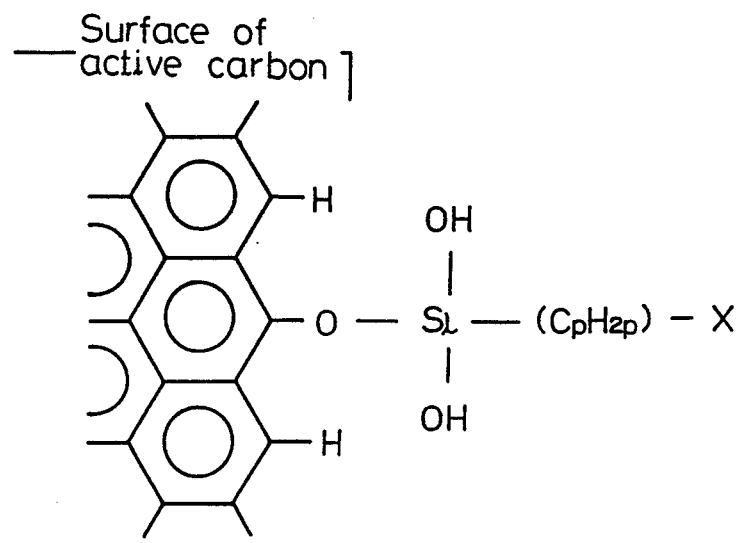
FIGS. 1 and 3 are diagrams illustrating examples of the silanol bond on the surface of an active carbon according to the present invention.
Figure 2:
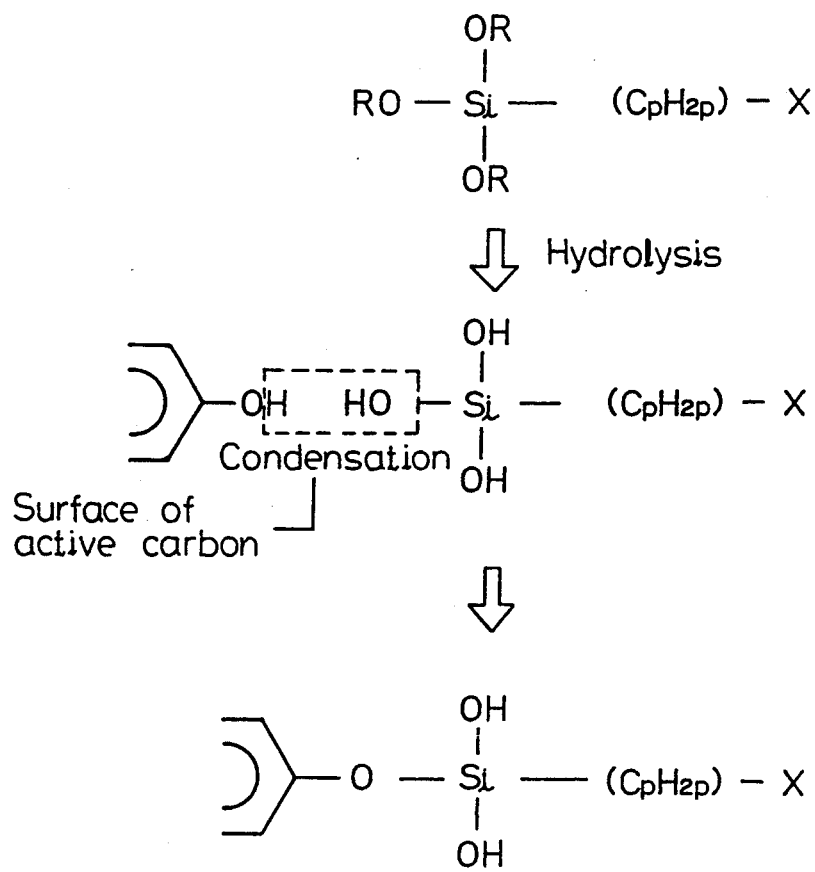
FIG. 2 is a formula representing a silanol bond-forming reaction according to the present invention; and, FIG. 4 is a reaction formula representing an adsorption mechanism model of an active carbon according to the present invention.

FIG. 1 illustrates an example of the silanol bond having a deodorizing functional group X fixed to the surface of the thus-obtained active carbon. The reaction for this bonding is shown in FIG. 2. In FIGS. 1 and 2, P is a positive integer, and —OR is a hydrolizable group.

As another example of the silanol bond of the present invention, there can be mentioned:

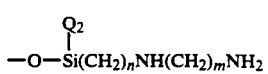

Wherein Q represents a hydroxyl group or a monovalent oxygen direct bond, n is an integer of from 1 to 5, and m is integer of from 1 to 5, and

wherein Q is as defined above, and k is an integer of from 1 to 5.

Figure 3:
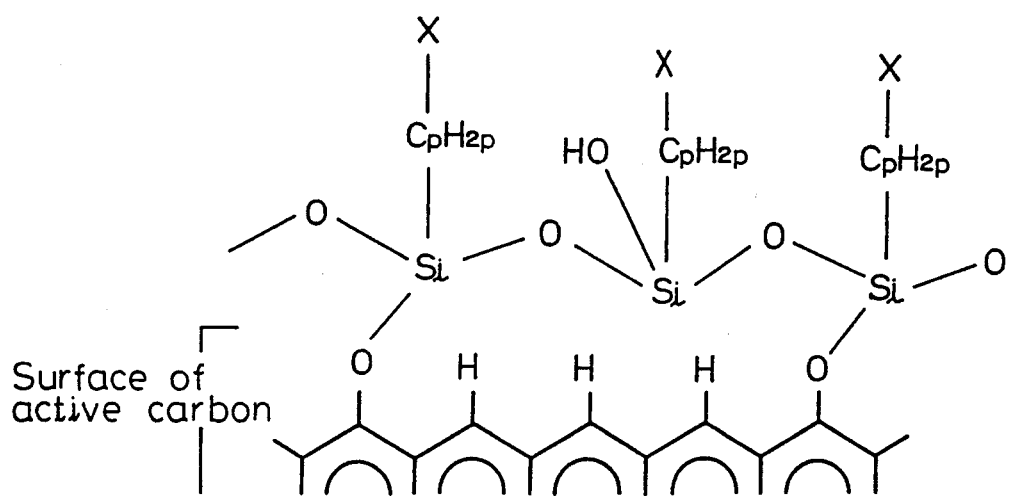

On the surface of the thus-obtained active carbon, as shown in FIG. 3, silanol groups are crosslinked by dehydration condensation through a siloxane bond —Si—O—Si—, and therefore, deodorizing functional groups can be introduced in a number larger than the number of hydroxyl groups on the surface of the active carbon. This siloxane crosslinkage has a deodorizing activity exceeding the active sites of the active carbon. For this reason also, the deodorizing performance can be advantageously improved.

The presence of a hydroxyl group on the surface of active carbon is essential for subjecting the silanol group of the silicon compound to dehydration condensation reaction. Accordingly, it is necessary that a hydroxyl group should be introduced in the surface of active carbon. An ozone treatment, an aqueous hydrogen peroxide treatment and the like can be mentioned as the means for introducing a hydroxyl group on the surface of active carbon. The introducing means is not limited to these methods, however, and any method capable of oxidizing the surface can be adopted.

The functional group-containing compound to be used for the introduction of a deodorizing functional group on the surface of active carbon is typically a silicon compound, as shown in FIG. 2, having a hydrolyzable group, which is hydrolyzed in water to form a silanol group, on one hand, and having a deodorizing functional group (especially an amino group) on the other hand.

An alkoxy group, an acetoxy group and the like can be utilized as the hydrolyzable group —OR.

An amino group, a sulfone group and the like are excellent as the deodorizing functional group, and a primary amine group is especially preferably used. The amino group is especially effective for deodorizing a harmful gas such as acetaldehyde or hydrogen sulfide, and the sulfone group is effective for deodorizing a basic gas such as ammonia or an amine.

As the silicon compound having both a deodorizing functional group and a silanol bond-forming group, there can be mentioned compounds represented by the following formulae:

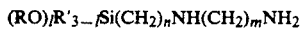

and

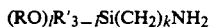

wherein R independently represents a hydrogen atom or an alkyl group having 1 to 5 carbon atoms, R' independently represents an alkyl group having 1 to 5 carbon atoms, l is an integer of from 1 to 3, n is an integer of from 1 to 5, m is an integer of from 1 to 5, and k is an integer from 1 to 5.

Since the alkoxy group forms an alcohol and the acetoxy group forms a fatty acid under hydrolysis conditions, sometimes the aqueous solution has a slight smell. Accordingly, a compound having an alkoxy group having a reduced smell is practically preferably used, but this smell has no influence on the deodorizing performance (bad smelling gas-adsorbing capacity).

As specific examples of the alkoxy group-containing silicon compound having an amino group, there can be mentioned N-β(aminoethyl)-γ-aminopropyltrimethoxysilane[(H$_3$CO)$_3$SiC$_3$H$_6$NHC$_2$H$_4$NH$_2$], N-β(aminoethyl)-γ-aminopropyltrimethoxysilane[(H$_3$CO)$_2$-SiC$_3$H$_6$NHC$_2$H$_4$NH$_2$], γ-aminopropyltriethoxysilane[(H$_5$C$_2$O)$_3$SiC$_3$H$_6$NH$_2$], and γ-aminopropyltrimethylsiloxysilane [(H$_3$CSiO)SiC$_3$H$_6$NH$_2$].

As pointed out hereinbefore, by the dehydration condensation of the silanol group formed in water by the hydrolysis and the hydroxyl group on the surface of the active carbon, a silanon bond Si—O—C is formed, and the deodorizing functional group of the deodorizing functional group-containing compound is fixed onto the active carbon by the chemical bonding.

For the production of the active carbon for deodorization according to the present invention, hydroxyl group-introduced active carbon is first prepared. At this step, the shape of active carbon is not particularly critical, and any of powdery, granular and fibrous shapes can be adopted. Then, the active carbon acting as the carrier is immersed in an aqueous solution of the deodorizing functional group-containing compound to sufficiently coordinate the deodorizing functional group-containing compound on the surface of the active carbon, and water is removed by suction filtration or centrifugal dehydration and the residue is dried. Alternatively, there can be adopted a process in which the above-mentioned aqueous solution is sprayed onto the active carbon, and then the active carbon is dried. At the drying step, a dehydration condensation occurs and the deodorizing functional group is fixed onto the surface of the active carbon through the silanol bond. At this step, deodorizing group-containing compounds together form a siloxane bond by the condensation of the silanol group and are crosslinked, as shown in FIG. 3. Therefore, the deodorizing functional group can be introduced in an amount larger than the hydroxyl group on the surface of the active carbon. Nevertheless, even if the deodorizing functional group-containing compound is fixed onto the active carbon in an unnecessarily large amount, a multiple-later crosslinkage is three-dimensionally formed, and therefore, sometimes the introduced deodorizing functional group is not satisfactorily utilized. In the active carbon for deodorization according to the present invention, the amount of the deodorizing functional compound fixed to the active carbon is 5 to 100% by weight, preferably 5 to 55% by weight, of the weight of the active carbon.

The active carbon for deodorization can be directly used as a material, and furthermore, the active carbon can be used after molding into a filter or the like. The filter may be in the form of an unwoven fabric, a foam, a multiple-layer structure, a honeycomb, a corrugate or a sheet, though the shape is not particularly critical. As the molding method, there can be adopted not only a method in which the active carbon for deodorization is dry-molded, but also a wet molding method while utilizing the advantage that the deodorizing functional group is fixed by the chemical bonding. Of course, there also can be adopted a method in which the active carbon before an introduction of the deodorizing functional group is molded into the above-mentioned shape, and after immersion in the aqueous solution of the deodorizing functional group-containing compound, spraying of the aqueous solution or coating with the aqueous solution, the active carbon is dried.

Since a deodorizing functional group is introduced by utilizing the silanol bond in the active carbon for deodorization according to the present invention, this active carbon can be prepared much easier than according to the physical process (low-temperature plasma process or the like) of directly introducing a functional group or the chemical process (organic synthetic chemical process) utilizing a direct reaction. Especially where an amino group is utilized as the deodorizing functional group, not only a primary amino group having a high activity but also secondary and tertiary amino groups are formed according to the conventional processes, but according to the present invention, the amino group before introduction can be fixed on the surface of active carbon without any change of the amino group.

The fixed amino group shows an excellent deodorizing capacity by chemical adsorption to an acidic gas which is not substantially adsorbed by an active carbon, such as acetaldehyde or hydrogen sulfide. Furthermore, other functional groups can be similarly fixed, and the attainment of excellent deodorizing performances in the chemical adsorption of a basic gas can be expected.

Moreover, a dropping off of the ingredients does not occur during use, and the functional group is firmly fixed compared with the conventional deposition process, and therefore, the functional group is effectively utilized even if the amount introduced of the functional group is small, with the result that the deodorizing efficiency is improved. Moreover, in the product of the present invention, micropores of the active carbon for adsorption are substantially not embedded with the functional group, and the neutral gas-adsorbing property inherent to active carbon can be maintained at a high level. Still further, even if the treated active carbon of the present invention is wet-molded, the molded body is not damaged or degraded by water washing, and an integrally molded deodorant of the all-round type exerting a deodorizing effect on all neutral gases, acid gases and a basic gas can be provided according to the present invention.

EXAMPLES

The present invention will now be described in detail with reference to the following examples, that by no means limit the scope of the invention.

EXAMPLE 1

γ-Aminopropyltriethoxysilane, $H_2NC_3H_6Si(OC_2H_5)_3$, was used as the functional group compound to be fixed, and a hydroxyl group-introduced active carbon fiber having a specific surface area of 1200 m$^2$/g was used as the carrier. The hydroxyl group-introducing treatment was effected by spraying nitrogen containing ozone at a concentration of 2800 ppm to the active carbon fiber for about 15 minutes.

Then, the functional group compound was added to 100 l of water charged in a vessel to adjust the concentration to 0.05 to 50% by weight, and 1000 g of the carrier was immersed in the so-prepared treating solution. The standing time was adjusted to 10 minutes to 24 hours. Then a suction filtration was effected for dehydration, and the solid was maintained at 50° to 160° C. for 1 to 24 hours to fix the functional group. The amount of the functional group-containing compound deposited was 19% by weight of the weight of the carrier.

The adsorption performances of the products treated under various conditions were evaluated by a gas chromatograph (GC-9A supplied by Shimazu Seisakusho). Experiments were repeated to establish treatment conditions, and it was confirmed that preferred conditions were a treating solution concentration of 0.2% by weight, an immersion time of 30 minutes and a drying condition of 120° C./3 hours.

Figure 4:
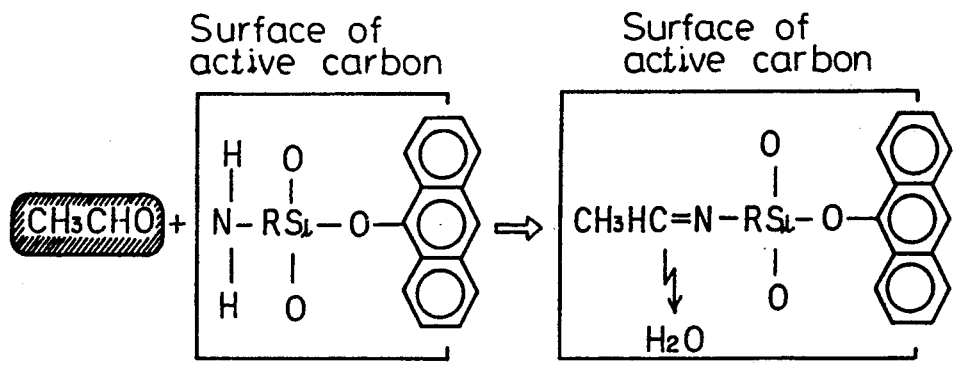

FIG. 4 shows a model of the mechanism of adsorption of acetaldehyde.

The above-mentioned optimum deposition conditions were determined in the following manner. The relationship among the immersion time, the drying temperature and the drying time was examined under factor conditions shown in Table 1, the obtained data shown in Table 2, and results of the analysis of the data shown in Table 3. As a result, it was confirmed that the factor having the largest influence on the acetaldehyde removal ratio was the drying temperature. When the factor effect was estimated, it was found that the mean values at factors B1 and B2, that is, drying temperatures of 80° C. and 120° C., were 99.8% and 92.7%, respectively, which were greatly different from 63.1% at B3 (drying temperature of 160° C.). From these results, it was understood that the optimum drying condition was 120° C./3 hours.

Regarding the results of an examination of treatment conditions such as the treating solution concentration, the factor table is shown in Table 4, the data are shown in Table 5, and the analysis results are shown in Table 6. From the dispersion results, it is seen that the treating solution concentration exerted a high contribution ratio. The mean acetaldehyde removal ratios at factors A1, A2 and A3 were 82.9%, 98.2% and 99.1%, respectively, and it is understood that at a treating solution concentration of 0.2%, a high removal ratio was attained. Furthermore, as the treating solution concentration increased, the toluene removal ratio tended to decrease. In view of the foregoing, it was construed that the optimum treating solution concentration was 0.2%.

TABLE 1

| Factor Table (deposition concentration fixed to 0.2%) | | | | |
|---|---|---|---|---|
| Factor | Level Number | 1 | 2 | 3 |
| A. immersion time | 3 | 10 minutes | 1 hour | 24 hours |
| B. drying temperature | 3 | 80° C. | 120° C. | 160° C. |
| C. drying time | 3 | 3 hours | 6 hours | 24 hours |

TABLE 2

| Orthogonal Table and Data | | | | | | |
|---|---|---|---|---|---|---|
| Sample No. | A | B | C | H$_2$S Removal ratio (%) | CH$_3$CHO Removal ratio (%) | C$_7$H$_8$ Removal ratio (%) |
| 1 | 1 | 1 | 1 | 100 | 99.5 | 69.1 |
| 2 | 1 | 2 | 2 | 87.9 | 94.0 | 68.5 |
| 3 | 1 | 3 | 3 | 37.7 | 43.5 | 64.4 |
| 4 | 2 | 1 | 2 | 100 | 100 | 60.5 |
| 5 | 2 | 2 | 3 | 74.2 | 87.7 | 62.7 |
| 6 | 2 | 3 | 1 | 43.3 | 72.7 | 53.8 |
| 7 | 3 | 1 | 3 | 98.9 | 100 | 64.2 |
| 8 | 3 | 2 | 1 | 97.4 | 96.4 | 60.2 |
| 9 | 3 | 3 | 2 | 46.5 | 73.0 | 64.1 |

TABLE 3

| | Dispersion Analysis Table | | | | | |
|---|---|---|---|---|---|---|
| | $H_2S$ Removal ratio | | $CH_3CHO$ Removal ratio | | $C_7H_8$ Removal ratio | |
| | dispersion ratio | contribution ratio | dispersion ratio | contribution ratio | dispersion ratio | contribution ratio |
| A. treating time | 3.13 | 1.34 | 1.43 | 1.94 | 4.93 | 48.74 |
| B. drying temperature | 150.14 | 93.87 | 17.51 | 74.27 | 1.14 | 1.70 |
| C. drying time | 4.62 | 2.28 | 2.29 | 5.80 | — | — |
| e | — | 2.52 | — | 18.00 | — | 49.57 |

TABLE 4

Factor Table (drying temperature fixed to 120° C.)

| Factor | Level Number | 1 | 2 | 3 |
|---|---|---|---|---|
| A. treating solution concentration | 3 | 0.1% | 0.2% | 0.4% |
| B. dehydrating condition | 3 | suction filtration, 30 seconds | natural filtration, 30 seconds | natural filtration, 15 seconds |
| C. ACF*/treating solution | 3 | 1.5 g/500 ml | 3.0 g/500 ml | 3.0 g/300 ml |
| D. treating temperature | 3 | 28° C. | 10° C. | 40° C. |

*)ACF: active carbon fiber

TABLE 5

Orthogonal Table and Data

| Sample No. | A | B | C | D | $H_2S$ Removal ratio (%) | $CH_3CHO$ Removal ratio (%) | $C_7H_8$ Removal ratio (%) |
|---|---|---|---|---|---|---|---|
| 1 | 1 | 1 | 1 | 1 | 93.5 | 95.6 | 68.2 |
| 2 | 1 | 2 | 2 | 2 | 69.2 | 81.8 | 70.7 |
| 3 | 1 | 3 | 3 | 3 | 49.0 | 71.2 | 77.0 |
| 4 | 2 | 1 | 2 | 3 | 98.5 | 98.9 | 63.6 |
| 5 | 2 | 2 | 3 | 1 | 82.2 | 95.8 | 74.6 |
| 6 | 2 | 3 | 1 | 2 | 100 | 100 | 63.9 |
| 7 | 3 | 1 | 3 | 2 | 100 | 98.3 | 54.9 |
| 8 | 3 | 2 | 1 | 3 | 82.7 | 100 | 47.6 |
| 9 | 3 | 3 | 2 | 1 | 100 | 98.9 | 53.8 |

Note Please refer to Table 1 of Example 1 for the measuring method.

TABLE 6

| | Dispersion Analysis Table | | | | | |
|---|---|---|---|---|---|---|
| | $H_2S$ Removal ratio | | $CH_3CHO$ Removal ratio | | $C_7H_8$ Removal ratio | |
| | dispersion ratio | contribution ratio | dispersion ratio | contribution ratio | dispersion ratio | contribution ratio |
| A. treating solution concentration | 2.83 | 28.75 | 7.34 | 53.27 | 103.41 | 86.71 |
| B. dehydration condition | 1.53 | 8.28 | 1.31 | 2.61 | — | — |
| C. ACF/treating solution | — | — | 2.25 | 10.52 | 12.28 | 9.55 |
| D. treating temperature | 1.01 | 0.17 | — | — | 1.42 | 0.36 |
| e | — | — | — | 33.60 | — | 3.39 |

The single-component gas removal performance as the effect is shown in Table 7, and it is clear that, in the product of the present invention, the removal ratio of an acidic gas such as acetaldehyde or hydrogen sulfide was superior to that of the untreated product.

To confirm that the fixing of the functional group was satisfactorily effected, the results obtained with respect to water-washed products are also shown in Table 7. The washed product (1) was obtained by placing the product in running water (10 l/min) for 24 hours, and the water-washed product (2) was obtained by placing the product in the same running water for 100 hours. It is seen that no degradation occurred even if water washing was conducted under these conditions.

TABLE 7

Single-Component Gas Removal Ratio

| | untreated product | treated product | water-washed product (1) | water-washed product (2) |
|---|---|---|---|---|
| acetaldehyde | 30.1 | 100 | 100 | 100 |
| hydrogen sulfide | 22.0 | 100 | 100 | 100 |
| toluene | 80.5 | 75.0 | 75.0 | 75.0 |

(Remarks)
Measurement method: gas chromatograph, circulation system (passage volume of 5 l), initial acetaldehyde concentration of 100 ppm, initial hydrogen sulfide concentration of 100 ppm, initial toluene concentration of 800 ppm, sample amount of 0.05 g, circulation time of 1 hour

EXAMPLE 2

The functional group compound and carrier used in Example 1 were used, and the amount deposited of the functional group compound was changed by changing the treating conditions. The performances of the obtained products are shown in Table 8.

The amount deposited was changed by changing the treating method to obtain products (1) through (8).

It was considered that in the treated product obtained in Example 1, the amount deposited was preferably about 19% by weight. It is seen that, in Example 2, if the amount deposited was in a range of from 5 to 55% by weight, the removal ratio of acetaldehyde or hydrogen sulfide was superior to that of the untreated product.

TABLE 8

Single-Component Gas Removal Ratio (%)

| | untreated product | Sample (1) | Sample (2) | Sample (3) | Sample (4) | Example 1 | Sample (5) | Sample (6) | Sample (7) | Sample (8) |
|---|---|---|---|---|---|---|---|---|---|---|
| acetaldehyde | 30.1 | 33.5 | 60.5 | 89 | 95 | 100 | 100 | 99 | 97 | 37.4 |
| hydrogen sulfide | 22.0 | 27.8 | 40.2 | 78 | 92 | 100 | 99 | 97 | 65 | 35.0 |
| toluene | 80.5 | 79.2 | 78.3 | 77.0 | 76.1 | 75.0 | 70.1 | 68.0 | 65.1 | 10.2 |
| deposited | 0 | 1% | 5% | 8% | 13% | 19% | 25% | 33% | 55% | 150% |

TABLE 8-continued

| | Single-Component Gas Removal Ratio (%) | | | | | | | | |
|---|---|---|---|---|---|---|---|---|---|
| | untreated product | Sample (1) | Sample (2) | Sample (3) | Sample (4) | Example 1 | Sample (5) | Sample (6) | Sample (7) | Sample (8) |
| amount (wt. %) | | | | | | | | | | |

Measurement method: same as in Example 1

EXAMPLE 3

Active carbon products were prepared according to the same treating method as described in Example 1, by using, instead of the functional group compound used in Example 1, (A) γ-glycidoxypropyltrimethoxysilane, (B) N-β(aminoethyl)-γ-aminopropyltrimethoxysilane, (C) dimethyltrimethylsilylamine, or (D) N-(β-aminoethyl)-γ-aminopropyltrimethoxysilane.

The obtained results are shown in Table 9. The obtained products are designated as treated products (A) through (D).

From the obtained results, it is seen that in the treated products (B), (C) and (D) having a functional group compound having a basic structure similar to that of the functional group compound used in Example 1, the removal ratios of acetoaldehyde and hydrogen sulfide, i.e., acidic gases, were much higher than that attained in the untreated product and were comparable to the performance of the treated product of Example 1. From the structure of the treated product (A), it is seen that, where a functional amino group making a contribution to adsorption of a gas was not contained in the functional group compound, no effect was attained. Accordingly, it is understood that an appropriate ingredient can be selected according to the kind of a gas to be adsorbed.

TABLE 9

| | Single-Component Gas Removal Performance | | | | | |
|---|---|---|---|---|---|---|
| | untreated product | treated product of Example 1 | treated product (A) | treated product (B) | treated product (C) | treated product (D) |
| acetaldehyde | 30.1% | 100 | 17.2 | 100 | 100 | 93.5 |
| hydrogen sulfide | 22.0 | 100 | 4.1 | 97.3 | 95.8 | 91.7 |
| toluene | 80.5 | 75.0 | 72.4 | 73.0 | 72.9 | 71.9 | measuring method: same as in Example 1

EXAMPLE 4

Powdery active carbon was treated as a carrier in the same manner as described in Example 1 by using the same functional group as used in Example 1. The results are shown in Table 10.

The obtained treated product was slightly inferior to the treated product of Example 1 with respect to removal ratios of acetaldehyde, hydrogen sulfide and toluene, but the removal ratios of acetaldehyde and hydrogen sulfide were much higher than those of untreated powdery active carbon. The specific surface area of the powdery active carbon used in this example was 700 m$^2$/g, which was smaller than 1200 m$^2$/g of the specific surface area of the active carbon fiber used in Example 1, but a definite effect of improving the adsorption performance was observed.

TABLE 10

| | Single-Component Gas Removal Ratio (%) | | | |
|---|---|---|---|---|
| | Example 1 | | Example 4 | |
| | untreated product | treated product | untreated product | treated product |
| acetaldehyde | 30.1 | 100 | 48.1 | 82.9 |
| hydrogen sulfide | 22.0 | 100 | 21.9 | 72.4 |
| toluene | 80.5 | 75.0 | 63.5 | 47.6 | measuring method: same as in Example 1

EXAMPLE 5

Deodorant sheets were formed by using the same functional group compound and carrier as used in Example 1.

Formed Sheet 1

The treated product of Example 1 was formed into a sheet by the known wet-forming method.

Formed Sheet 2

During the wet-forming method, the functional group compound was added to treat the carrier and a formed sheet was prepared.

Formed Sheet 3

The carrier was wet-formed into a sheet, and the sheet was coated with a solution of the functional group compound by spraying or the like, or the paper was dipped in the solution.

The performances of each formed product are shown in Table 11. Each of the formed sheets had a much higher removal ratio of acetaldehyde or hydrogen sulfide than the untreated paper.

The shape of the filter may be a nonwoven fabric, a sponge, a honeycomb and a corrugate, and the treating method shown in this example can be applied to any shape of filter.

TABLE 11

| | Single-Component Gas Removal Ratio (%) of Formed Product | | | |
|---|---|---|---|---|
| | untreated paper | formed sheet 1 | formed sheet 2 | formed sheet 3 |
| acetaldehyde | 40.5 | 100 | 99.9 | 98.0 |
| hydrogen sulfide | 30.2 | 100 | 100 | 99.8 |
| toluene | 99.5 | 98 | 97.0 | 97.5 | measuring method: same as in Example 1, sample amount 0.5 g, 10% of PVA contained as binder in paper

COMPARATIVE EXAMPLE 1

The treatment was carried out under the same preparation conditions as described in Example 1 by using, as the functional group compound to be fixed, (1) cyclic epoxymethoxysilane, (2) glycidoxymethoxysilane, (3) aminoethoxysilane, (4) uredopropyltriethoxysilane, (5) polyethoxydimethylsiloxane, (6) aminoethylaminopropyltrimethoxysilane, or (7) γ-aminopropylethoxysilane, and using a calcium whisker as the carrier. The treated products are designated as treated products (1) through (7). The results of an evaluation of the performances of these products are shown in Table 12.

As seen from these results, no effect was attained in the case of a carrier having a specific surface area smaller than 1 m²/g, though a slight improvement was attained by certain functional group compounds.

TABLE 13

Single-Component Gas Removal Ratios (%) of Product of Present Invention and Amine-Deposited Active Carbon

|  | untreated product | aromatic amine-deposited product primary amino group | aliphatic amine-deposited product tertiary amino group | Examples 2–6 primary amino group |
|---|---|---|---|---|
| acetaldehyde | 30.1 | 93.8 | 10.6 | 99.0 |
| hydrogen sulfide | 22.0 | 20.1 | 37.0 | 97.0 |
| toluene | 80.5 | 33.9 | 43.0 | 68.0 | measuring method: same as in Example 1 as a tobacco smoke. Moreover, a sweet stimulant smell left after the treatment of a tobacco smell with ordinary active carbon is not observed, and the smell can be moderated.

TABLE 12

Single-Component Gas Removal Ratio (%)

|  | untreated product | treated product (1) | treated product (2) | treated product (3) | treated product (4) | treated product (5) | treated product (6) | treated product (7) |
|---|---|---|---|---|---|---|---|---|
| acetaldehyde | 16.3 | 0.3 | 1.7 | 13.6 | 5.0 | 1.7 | 24.7 | 22.5 |
| hydrogen sulfide | 0.0 | 8.4 | 3.4 | 0.0 | 0.0 | 3.4 | 1.7 | 0.3 |
| toluene | 1.3 | 0.0 | 0.0 | 0.0 | 2.7 | 0.0 | 7.5 | 1.6 | measuring method: same as in Example 1

COMPARATIVE EXAMPLE 2

Amine-deposited active carbon fibers were obtained by immersing the same active carbon fibers as used in Examples 1 through 3 in aqueous solutions containing 0.5% by weight of an aromatic amine having a primary amino group or an aliphatic amine having a tertiary amino group, and drying the immersed active carbon fibers.

The single-component gas removal ratios of the obtained fibers were measured according to the same method as described in Example 1. Simultaneously, the performances of the product of the present invention (sample 6 of Example 2), obtained by immersing a hydroxyl group-introduced active carbon fiber in an aqueous solution containing 0.5% by weight of γ-aminopropyltriethoxysilane and drying the immersed carbon fiber are shown in Table 13.

From the acetaldehyde removal ratios shown in Table 13, it is seen that the primary amino group is superior to the tertiary amino group as the deodorizing functional group, from the viewpoint of the adsorbing capacity. The product of the present invention having amino groups firmly fixed thereto has a superior acidic gas removal ratio to that of mere deposited active carbon, and the degree of reduction of the removal ratio of toluene, which is a neutral gas, is maintained at a low level. Accordingly, the product of the present invention is especially effective for deodorizing a mixed gas comprising an acidic gas, a neutral gas and a basic gas, such

We claim:

1. An active carbon for deodorization, which comprises a deodorizing functional group fixed to a graphitic six-membered ring on the surface of an active carbon through a silanol bond.

2. An active carbon for deodorization according to claim 1, wherein the deodorizing functional group is at least one member selected from the group consisting of amino groups and sulfone groups.

3. An active carbon for deodorization according to claim 2, wherein the deodorizing functional group is a primary amino group.

4. An active carbon for deodorization according to claim 1, wherein the group fixed to the graphitic six-member ring is a group of the formula:

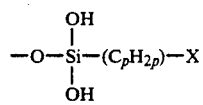

wherein X is a deodorizing functional group, and p is a positive integer.

5. An active carbon for deodorization according to claim 1, wherein the group fixed to the graphitic six-member ring is a group selected from the group consisting of:

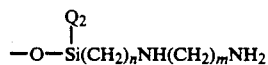

wherein Q represents a hydroxyl group or a monovalent oxygen direct bond, n is an integer of from 1 to 5, and m is integer of from 1 to 5, and

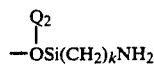

where Q as defined above, and k is an integer of from 1 to 5.

6. An active carbon for deodorization according to claim 1, wherein the amount of the deodorizing functional group deposited is 5 to 100% by weight of the weight of the active carbon.

7. A process for the preparation of an active carbon for deodorization, which comprises steps of forming a hydroxyl group on graphitic active carbon on a surface of the active carbon by an oxidation treatment, and condensing said hydroxyl group formed on the surface of the active carbon with a silicon compound having a hydrolyzable group and a deodorizing functional group, to thereby fix the deodorizing functional group to the surface of the active carbon through a silanol bond.

8. A process according to claim 7, wherein the deodorizing functional group is a member selected from the group consisting of amino groups and sulfone groups.

9. A process according to claim 8, wherein the deodorizing functional group is a primary amino group.

10. A process according to claim 7, wherein the silicon compound is a compound of the formula:

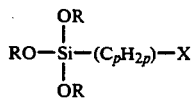

wherein X is a deodorizing functional group, p is a positive integer, and —OR is a hydrolizable group.

11. A process according to claim 7, wherein the silicon compound is a member selected from the group consisting of compounds represented by the following formula:

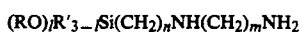

wherein R independently represents a hydrogen atom or an alkyl group having 1 to 5 carbon atoms, R' independently represents an alkyl group having 1 to 5 carbon atoms, l is an integer of from 1 to 3, n is an integer of from 1 to 5, and m is an integer of from 1 to 5, and compounds represented by the following formula:

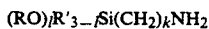

wherein R, R' and l are as defined above, and k is an integer of from 1 to 5.

* * * * *